United States Patent [19]

Amento et al.

[11] Patent Number: 5,753,623
[45] Date of Patent: May 19, 1998

[54] METHOD OF TREATMENT FOR DEPRESSION

[75] Inventors: Edward P. Amento, Portola Valley; Eugene A. Bauer, Los Altos, both of Calif.

[73] Assignee: Connetics Corporation, Palo Alto, Calif.

[21] Appl. No.: 475,004

[22] Filed: Jun. 7, 1995

[51] Int. Cl.$^6$ .............................. A61K 38/00; C07K 5/00; C07K 7/00; C07K 16/00
[52] U.S. Cl. .................... 514/12; 514/21; 530/324
[58] Field of Search .................... 514/12, 21; 530/324

[56] References Cited

U.S. PATENT DOCUMENTS 5,108,897  4/1992  Steinetz et al. .................. 435/7.9
5,166,191  11/1992  Cronin et al. .................... 514/12

Primary Examiner—Cecilia J. Tsang
Assistant Examiner—Jennifer Harle
Attorney, Agent, or Firm—David A. Lowin, Esq.

[57] ABSTRACT

Depression, particularly disease- and medical treatment-related depression, and especially postpartum depression, is treated by the administration of a therapeutically effective amount of relaxin. A treatment regimen and dosage form for gradual withdrawal from relaxin therapy is also disclosed.

13 Claims, 1 Drawing Sheet

Serum relaxin concentrations (ng/mL)
after a single sc dose of 10 mcg/kg

• observed data
—— fitted curve

METHOD OF TREATMENT FOR DEPRESSION

FIELD OF THE INVENTION

The present invention relates to treatments for depression and/or anxiety, particularly for disease- and medical treatment-related depression, and for postpartum depression, and specifically to such a treatment employing the administration of relaxin.

BACKGROUND INFORMATION

As described in *Textbook of INTERNAL MEDICINE*, Kelley, et al. (eds.), Part X: Neurology, Chapter 469: Major Psychiatric Disorders, (J. Lippincott Co., Philadelphia), pp. 2198–2199 (1992), unipolar affective disorder (i.e., depression without episodes of mania or "major depression") can occur throughout life and is at least twice as common in women as in men. Patients often present without the subjective sense of being depressed but complaining of somatic symptoms of depression, most commonly fatigue, sleep disturbances, or impotence. Patients may describe feeling sad, blue, low, irritable, or anxious, as well as being depressed. Diagnosis of major depression is based either on a distinct change of mood that is prominent, generally persists throughout the day, and occurs each day for at least 2 weeks or on markedly diminished interest or pleasure in most activities over a similar period. The diagnosis requires that at least four of the following symptoms be present nearly every day for a period of 2 weeks: significant weight loss (or weight gain in some younger patients), prominent sleep disturbance, agitation or retardation with slow speech, fatigue, feelings of worthlessness and guilt, slowed thinking, and hopelessness.

Depression can likewise be associated with the symptoms of disease (e.g., systemic lupus erythematosus) or as a side effect of the treatment of disease (e.g., with antihypertensive therapy). One form of depression, postpartum depression, has been commonly found in women during the period following childbirth.

Mature human relaxin is a hormonal peptide of approximately 6000 daltons known to be responsible for remodelling the reproductive tract before parturition, thus facilitating the birth process. This protein appears to modulate the restructuring of connective tissues in target organs to obtain the required changes in organ structure during pregnancy and parturition. See, Hisaw, F. L., *Proc. Soc. Exp. Biol. Med.*, 23: 661–663 (1926); Schwabe, C., et al., *Biochem. Biophys. Res. Comm.*, 75: 503–570 (1977); James, R. et al., *Nature*, 267: 544–546 (1977). A concise review of relaxin was provided by Sherwood, D. in *The Physiology of Reproduction*, Chapter 16, "Relaxin", Knobil, E. and Neill, J., et al. (eds.), (Raven Press Ltd., New York), pp. 585–673 (1988). Circulating levels of relaxin are elevated for the entire nine months of pregnancy and drop quickly following delivery.

While predominantly a hormone of pregnancy, relaxin has also been detected in the non-pregnant female as well as in the male. Bryant-Greenwood, G. D., *Endocrine Reviews*, 3: 62–90 (1982) and Weiss, G., *Ann. Rev. Physiol.*, 46:43–52 (1984).

Relaxin has been purified from a variety of species including porcine, murine, equine, shark, tiger, rat, dogfish and human, and shows at least primary and secondary structural homology to insulin and the insulin-like growth factor. In the human, relaxin is found in most abundance in the corpora lutea (CL) of pregnancy. However, specific nuclei in the brain have relaxin receptors and other nuclei contain messenger RNA for relaxin. Several nuclei with cells bearing relaxin receptors are found in the area of the hypothalamus.

Two human gene forms have been identified, (H1) and (H2). Hudson, P., et al., *Nature*, 301: 628–631 (1983); Hudson, P., et al., *The EMBO Journal*, 3: 2333–2339 (1984); and U.S. Pat. Nos. 4,758,516 and 4,871,670. Only one of the gene forms (H2) has been found to be transcribed in CL. It remains unclear whether the (H1) form is expressed at another tissue site, or whether it represents a pseudo-gene. When synthetic human relaxin (H2) and certain human relaxin analogs were tested for biological activity, the tests revealed a relaxin core necessary for biological activity as well as certain amino acid substitutions for methionine that did not affect biological activity. Johnston, et al., in *Peptides: Structure and Function, Proc. Ninth American Peptide Symposium*, Deber, C. M., et al. (eds.) (Pierce Chem. Co. 1985).

Methods of making relaxin are also described in U.S. Pat. No. 4,835,251 and in co-pending U.S. Ser. Nos. 07/908,766 (PCT US90/02085), now U.S. Pat. No. 5,464,756 and 08/080,354 (PCT US94/0699). Methods of using relaxin in cardiovascular therapy and in the treatment of neurodegenerative diseases are described in U.S. Pat. No. 5,166,191 and in U.S. Ser. No. 07/902,637 (PCT US92/06927). Certain formulations of human relaxin are described in allowed U.S. Ser. No. 08/050,745 now U.S. Pat. No. 5,451,572.

Recombinant human relaxin (H2) in currently in Phase I human clinical trials in scleroderma patients. Scleroderma is a disease involving an imbalance in tissue reformation giving rise to the overproduction of collagen, and ultimately resulting in swelling and hardening of the skin (and affected organs). It has surprisingly been discovered that during treatment of scleroderma with relaxin, mood elevations corresponded to peak dosing periods and that discontinuation of therapy resulted in malaise described as best comparable to postpartum depression, which was reversible upon resumption of treatment.

SUMMARY OF THE INVENTION

In one aspect, the invention relates to a method of treating depression in a mammal in need thereof by administering a therapeutically effective amount of relaxin. In a preferred embodiment, relaxin is administered in an amount sufficient to maintain a serum concentration of at least about 1 ng/ml. In a further preferred embodiment the relaxin is recombinant human relaxin (H2).

In a preferred aspect of the invention, the depression is medical treatment-related or disease-related depression. In a further preferred embodiment, the depression is postpartum depression and the invention provides for a treatment regimen of initially administering an amount sufficient to maintain a pregnancy-level serum concentration of at least about 1 ng/ml of relaxin for an initial period, followed by gradually reducing the dosage over a period of time to maintain a normal non-pregnancy-level serum concentration of relaxin.

In another aspect of the invention, a sustained/controlled release relaxin formulation is provided having a selectively permeable outer barrier with a drug dispensing opening, a first inner relaxin-containing portion designed for steady state release of relaxin at a therapeutically effective daily dosage, and a second inner relaxin-containing portion designed to deliver relaxin at a predetermined progressively diminishing rate, commencing upon exhaustion of relaxin from the first inner portion.

In still another aspect of the invention, a sustained/controlled release relaxin formulation is provided having a selectively permeable outer barrier with a drug dispensing opening, and an inner relaxin-containing portion designed to deliver relaxin at a predetermined progressively diminishing rate.

DETAILED DESCRIPTION OF THE INVENTION

Definitions and General Parameters

Figure 1:
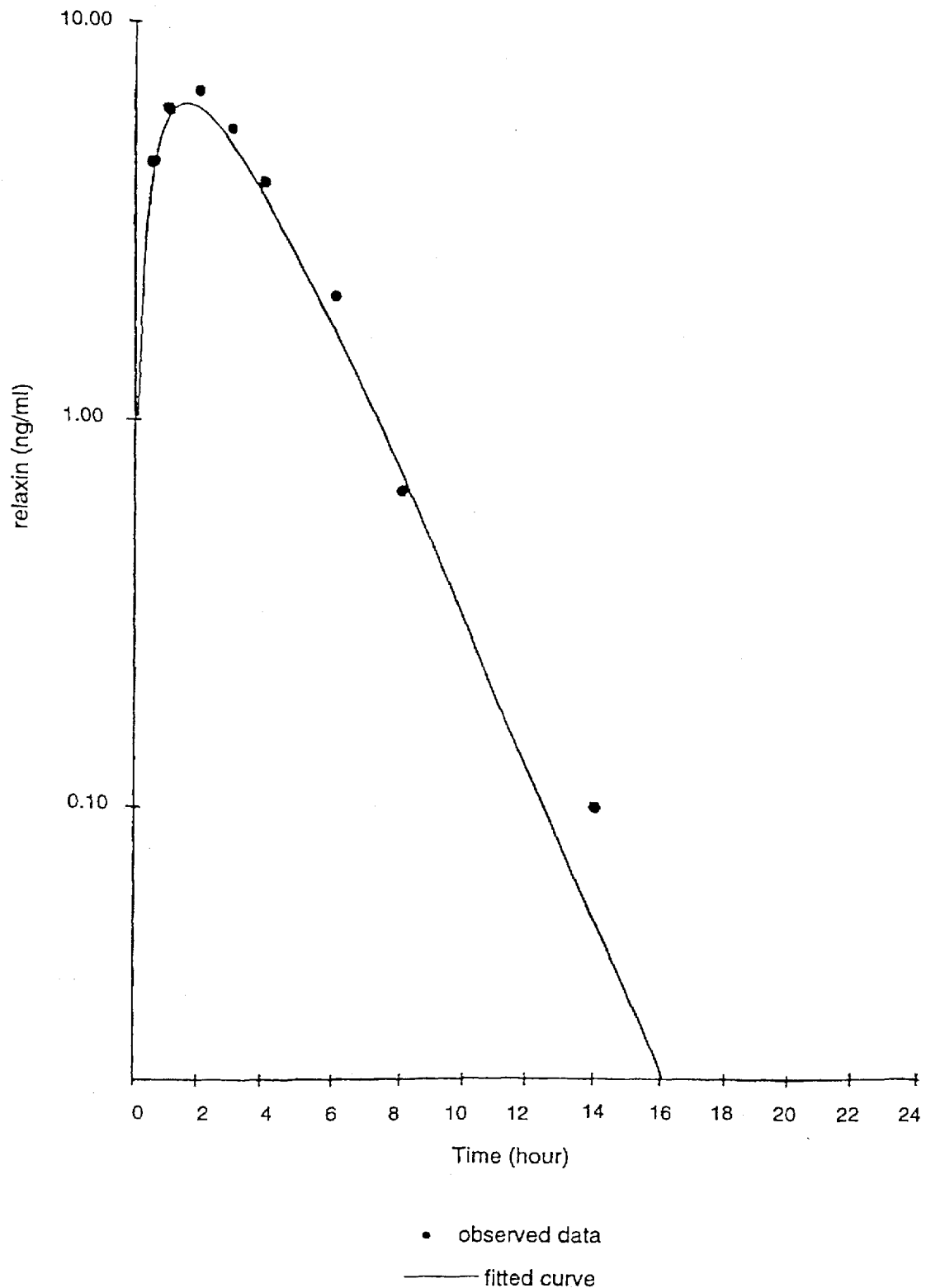
FIG. 1 is a graph showing serum relaxin concentration (ng/ml) as measured against time after administration of a single subcutaneous dose of 10 µg/kg to a scleroderma patient.

As used in the present specification, the following words and phrases are generally intended to have the meanings as set forth below, except to the extent that the context in which they are used indicates otherwise.

"Optional" or "optionally" means that the subsequently described event or circumstance may or may not occur, and that the description includes instances where said event or circumstance occurs and instances in which it does not.

The term "depression," particularly when used alone, is intended to encompass, but not be limited to, major depression, bipolar depression and/or anxiety, particularly disease-related depression (e.g., associated with scleroderma, systemic lupus erythematosus, Alzheimers) and postpartum depression.

The term "treatment" or "treating" means any therapeutic intervention in a mammal, including:

(i) preventing depression, that is, causing the clinical symptoms not to develop;

(ii) inhibiting depression, that is, arresting the development of clinical symptoms; and/or (iii) relieving depression, that is, causing the regression of clinical symptoms.

The term "effective amount" means a dosage sufficient to provide treatment for the disease state being treated. This will vary depending on the patient, the disease and the treatment being effected.

The term "relaxin" means human relaxin, including intact full length relaxin or a portion of the relaxin molecule that retains biological activity [as described in U.S. Pat. No. 5,023,321, preferably recombinant human relaxin (H2)] and other active agents with relaxin-like activity, such as Relaxin Like Factor (as described in co-pending application Ser. No. 08/484,219, Attorney Docket No. 1031, entitled "RELAXIN LIKE FACTOR AND METHODS AND USES THEREFOR"), relaxin analogs (as described in co-pending application Ser. No. 08/483,736, Attorney Docket No. 1036, entitled "RELAXIN ANALOG AND METHODS AND USES THEREOF") and agents that competitively displace bound relaxin from a receptor. Relaxin can be made by any method known to those skilled in the art, preferably as described in U.S. Pat. No. 4,835,251 and in co-pending U.S. Ser. Nos. 07/908,766 (PCT US90/02085) and 08/080,354 (PCT US94/0699).

Utility, Testing and Administration

Utility

Depression, particularly disease-related depression (e.g., depression associated with scleroderma, systemic lupus erythematosus, Alzheimers) and postpartum depression, is treated by the administration of a therapeutically effective amount of relaxin.

Relaxin is currently the subject of Phase I clinical trials involving scleroderma patients. Scleroderma is a disease involving an imbalance in tissue reformation giving rise to the overproduction of collagen, and ultimately resulting in swelling and hardening of the skin (and affected organs). Part of the clinical testing of relaxin in scleroderma patients included the monitoring of overall wellbeing. It has been observed during treatment of scleroderma with relaxin, that mood elevations corresponded to peak dosing periods and that discontinuation of therapy resulted in malaise described as best comparable to postpartum depression, which was reversible upon resumption of treatment.

Testing

In vivo activity for treating depression is determined according to several animal models, such as: the forced swimming wheel test described by Kasahara, et al., *Life Sci.*, 52(22):1741–1749 (1993); the tail suspension test described by Teste, et al., *Fundam. Clin. Pharmacol.*, 7(5):219–226 (1993); and in the Flinders sensitive line rats: a genetic animal model of depression described by Overstreet, *Neurosci. Biobehav. Rev.*, 17(1):51–68 (Spring 1993).

Human clinical trials for the treatment of depression are well known in the art, preferably in blinded studies evaluating subjects provided with blinded samples of the test active agent or placebo, and as described below in the Examples.

Administration

Relaxin is administered at a therapeutically effective dosage, e.g., a dosage sufficient to provide treatment for depression. Administration of relaxin can be via any of the accepted modes of administration for agents that serve similar utilities, preferably by systemic administration.

While human dosage levels for treating depression have yet to be optimized for relaxin, generally, a daily dose is from about 0.1 to 500.0 µg/kg of body weight per day, preferably about 6.0 to 200.0 µg/kg, and most preferably about 12.0 to 100.0 µg/kg. Generally it is sought to obtain a serum concentration of relaxin approximating or greater than normal circulating levels in pregnancy, i.e., 1.0 ng/ml, such as 0.5 to 50 ng/ml, preferably 1.0 to 20 ng/ml. In the ongoing clinical trials, dosages of about 6.0 µg/kg, 12.0 µg/kg and 50 µg/kg have respectively resulted in serum concentrations of about 1.8 ng/ml±0.3, 3.6 ng/ml±0.6, and 11.8 ng/ml±1.6. Thus, for administration to a 70 kg person, the dosage range would be about 7.0 µg to 3.5 mg per day, preferably about 42.0 µg to 2.1 mg per day, and most preferably about 84.0 to 700.0 µg per day. The amount of relaxin administered will, of course, be dependent on the subject and the severity of the affliction, the manner and schedule of administration and the judgment of the prescribing physician. One treatment regimen can employ a higher initial dosage level (e.g., 100 to 200 µg/kg/day) followed by decreasing dosages to achieve steady relaxin serum concentration of about 1.0 ng/ml. Another treatment regimen, particularly for postpartum depression, entails administration of an amount of relaxin sufficient to attain normal pregnancy levels of relaxin (about 1.0 ng/ml) followed by gradual decreasing dosages until relaxin serum levels are no longer detectable (e.g., less than about 20 pg/ml), optionally discontinuing treatment upon reaching that dosage level.

In employing relaxin for treatment of the above conditions, any pharmaceutically acceptable mode of administration can be used. Relaxin can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Relaxin can also be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and relaxin. In addition, these compositions may include other active agents, carriers, adjuvants, etc. Generally, depending on the intended mode of administration, the pharmaceutically acceptable composition will contain about 0.1% to 90%, preferably about 0.5% to 50%, by weight of relaxin, the remainder being suitable pharmaceutical excipients, carriers, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The formulations of human relaxin described in U.S. Ser. No. 08/050,745 are particularly preferred.

Parenteral administration is generally characterized by injection, either subcutaneously, intradermally, intramuscularly or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of relaxin contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably the composition will comprise 0.2–2% of the relaxin in solution.

A more recently devised approach for parenteral administration employs the implantation of a slow-release or sustained-release system, such that a constant level of dosage is maintained. Various matrices (e.g., polymers, hydrophilic gels, and the like) for controlling the sustained release, and for progressively diminishing the rate of release of active agents such as relaxin are known in the art. See, U.S. Pat. Nos. 3,845,770 (describing elementary osmotic pumps); 3,995,651, 4,034,756 and 4,111,202 (describing miniature osmotic pumps); 4,320,759 and 4,449,983 (describing multichamber osmotic systems referred to as push-pull and push-melt osmotic pumps); and 5,023,088 (describing osmotic pumps patterned for the sequentially timed dispensing of various dosage units).

In a preferred aspect of the invention, a sustained/controlled release relaxin formulation has a selectively permeable outer barrier with a drug dispensing opening, and an inner relaxin-containing portion designed to deliver a dosage of relaxin progressively diminishing at a predetermined rate (e.g., containing about 30 mg of relaxin in a matrix for delivery of initially about 500 µg per day diminishing at a rate of 10 µg per day).

In another preferred aspect of the invention, a sustained/controlled release relaxin formulation has a selectively permeable outer barrier with a drug dispensing opening, a first inner relaxin-containing portion designed for steady state release of relaxin at a therapeutically effective daily dosage (e.g., containing about 50 mg of relaxin in a matrix for continuous delivery of about 500 µg per day), and a second inner relaxin-containing portion designed to deliver a dosage of relaxin progressively diminishing at a predetermined rate (e.g., containing about 3 mg of relaxin in a matrix for delivery of initially about 500 µg per day diminishing at a rate of 50 µg per day) commencing upon exhaustion of the relaxin from the first inner portion.

Formulations of relaxin may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838, which discloses a method of administration for insulin that can be adapted for the administration of relaxin in the present invention.

EXAMPLES

The following preparations and examples are given to enable those skilled in the art to more clearly understand and to practice the present invention. They should not be considered as limiting the scope of the invention, but merely as being illustrative and representative thereof.

Example 1

Mouse Forced Swimming Wheel Model

This is a modification of the forced swimming wheel test described by Kasahara, et al., *Life Sci.*, 52(22):1741–1749 (1993).

Male Lewis mice are divided into control and treatment groups. Two hours before the test, the control and treatment groups, respectively, receive subcutaneous injections of placebo or 50 µg/kg/day of recombinant human relaxin (H2) formulated as described in allowed U.S. Ser. No. 08/050, 745. The mice are individually placed in the swimming wheel and the number of turns of the wheel is recorded for each. Antidepressant activity is indicated by an increased number of turns in the treatment group.

By following the above-described procedure, the relaxin treated group have an increased number of turns as compared to the control group, indicating antidepressant activity.

Example 2

Serum Relaxin Concentrations After Subcutaneous Administration

Relaxin (10 µg/kg) was administered as a single subcutaneous injection to a scleroderma patient. Blood samples were obtained at timed intervals and measured for serum relaxin concentration (ng/ml). The one-dose serum concentration data are shown in FIG. 1. Peak serum concentration was attained at about 2 hours post dosing. The dose curve is similar to that achieved with normal volunteers.

Example 3

Human Antidepressant Activity

A patient diagnosed as having severe systemic scleroderma with systemic sclerosis, was undergoing compassionate use therapy with relaxin. In a dose ranging phase of the therapy, recombinant human relaxin (H2) in a buffered citrate solution adjusted to Ph 5.0 was administered as a bolus subcutaneous injection of 0.5 mg.

At about two hours post dosing (a time approximating peak relaxin serum concentration as described in Example 2) the patient reported a significant improvement in wellbeing. As compared to her usual reduced activity typical of a normal functioning scleroderma sufferer, the patient expressed the strength, ability and desire to engage in more strenuous manual activities (otherwise described as "nesting").

At about seven hours post dosing (a time approximating relaxin serum concentration below 1 ng/ml) the patient reported significant anxiety/depression-like symptoms which she described as "the blues," relating that the closest experience she could describe was the postpartum depression she had experienced after childbirth.

Relaxin serum concentration correlates to the alleviation of depression.

Example 4

Human Antidepressant Activity

A patient diagnosed as having severe systemic scleroderma with systemic sclerosis, was undergoing compassionate use therapy with relaxin. She was being treated with 1.5 mg per day of recombinant human relaxin (H2) in a buffered citrate solution adjusted to pH 5.0. divided into six equal doses by subcutaneous injection to achieve a circulating concentration of about 1.0 ng/ml.

The patient inadvertently missed several doses of relaxin. In the wake of these failures, the patient experienced feelings similar to those she had previously experienced in the postpartum period; i.e., in her words, she had the "blues." This cleared within hours of readministration of relaxin.

The withdrawal and resumption of relaxin treatment was repeated and similar symptoms were experienced.

Over the course of the following year, during which the patient was not withdrawn from relaxin treatment, no similar episodes of depression were experienced.

Precipitous withdrawal from relaxin treatment correlates to depression, which can be reversed upon the re-administration of relaxin.

Example 5

Relaxin Treatment Regimen

Relaxin is administered in patient-dependent doses (about 6 µg/kg) sufficient to maintain serum concentrations of at least about 1.0 ng/ml (approximating relaxin concentration during pregnancy). Upon remission of the symptoms for which the patient is being treated, relaxin dosage levels are gradually decreased until the minimum dose level that maintains remission of symptoms is reached, (which will be patient-dependent, about 0.1 to 1.5 µg/kg of relaxin, or withdrawal from treatment upon successful titration of the dosage to zero).

Patients treated according to the above-described regimen do not experience depression associated with precipitous withdrawal from relaxin.

Example 6

Clinical Trial for Treatment of Postpartum Depression

One hundred pregnant female subjects are monitored for relaxin serum concentration during the course of their pregnancy. The subjects are randomized and divided into treatment and control groups. Three days after childbirth, in the treatment group, relaxin is administered by subcutaneous placement of a relaxin-containing osmotic pump delivering 50 µg/kg/day of recombinant human relaxin (H2); in the control group, placebo is administered by subcutaneous placement of a placebo-containing osmotic pump. The subjects are required to maintain a diary documenting their mood (e.g., joy/euphoria/depression/anxiety) over a period of three months following placement of the drug/placebo. The same is documented, along with relaxin serum concentration, by weekly visits to the treating physician.

The subjects in the relaxin-treated group show fewer signs of postpartum depression than the subjects in the control group.

Example 7

Relaxin Controlled Release Osmotic Pump

A sustained/controlled release relaxin osmotic pump has a selectively permeable outer membrane with a drug dispensing opening, a chamber containing 50 mg of recombinant human relaxin (H2) in a matrix for steady state release at a rate of 500 µg per day, surrounding a center chamber containing 3.0 mg of recombinant human relaxin (H2) in a matrix for delivering a dosage progressively diminishing at a rate of 50 µg per day, starting from 500 µg per day, upon exhaustion of relaxin from the surrounding chamber.

Example 8

Clinical Trial of Relaxin Controlled Release Osmotic Pump

One hundred subjects receiving relaxin treatment are randomized and divided into treatment and control groups. In the treatment group, relaxin is administered by subcutaneous placement of a relaxin-containing osmotic pump as described in Example 6; in the control group relaxin is administered by subcutaneous placement of a standard relaxin-containing osmotic pump delivering 500 µg/day of recombinant human relaxin (H2). The subjects are required to maintain a diary documenting their mood (e.g., joy/ euphoria/depression/anxiety) over a period of four months following placement of the drug. The same is documented, along with relaxin serum concentration, by weekly visits to the treating physician over the first 100 days, followed by daily visits from day 100 through the end of the fourth month.

Patients in the treatment group do not experience depression associated with precipitous withdrawal from relaxin, particularly as compared to the control group.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A method for treating depression in a mammal in need thereof comprising administering a therapeutically effective amount of relaxin, wherein said depression is major depression, bipolar depression, depression-related anxiety, postpartum depression or disease-related depression where the disease is scleroderma or systemic lupus erythematosus.

2. The method of claim 1 comprising the administration of relaxin in an amount sufficient to maintain a serum concentration of at least about 1 ng/ml.

3. The method of treatment of claim 1 comprising the administration of recombinant human relaxin (H2).

4. The method of treatment of claim 2 comprising the administration of recombinant human relaxin (H2).

5. The method of treatment of claim 3 wherein said relaxin is administered parenterally.

6. The method of claim 5 wherein said relaxin is administered by subcutaneous injection.

7. The method of treatment of claim 3 wherein said relaxin is administered by inhalation to the respiratory tract.

8. The method of treatment of claim 3 wherein said relaxin is administered topically in a transcutaneous electrotransport formulation adapted for application as a skin patch.

9. The method of treatment of claim 3 wherein said depression is disease-related depression where the disease is scleroderma or systemic lupus erythematosus.

10. The method of treatment of claim 9 wherein the disease is scleroderma.

11. The method of treatment of claim 3 wherein said depression is postpartum depression.

12. The method of claim 11 comprising the administration of relaxin in an amount sufficient to maintain a pregnancy-level serum concentration of at least about 1 ng/ml.

13. The method of claim 11 comprising a regimen of initially administering an amount sufficient to maintain a pregnancy-level serum concentration of at least about 1 ng/ml of relaxin for an initial period, followed by gradually reducing the dosage over a period of time to maintain a normal non-pregnancy-level serum concentration of relaxin.

* * * * *